US011839746B2

(12) United States Patent
Le Baccon et al.

(10) Patent No.: US 11,839,746 B2
(45) Date of Patent: Dec. 12, 2023

(54) ADAPTABLE IMAGE CAPTURE DEVICE AND SYSTEM FOR THE SECURE PRODUCTION OF MEDICINAL PREPARATIONS

(71) Applicant: EUREKAM, Lagord (FR)

(72) Inventors: Gaël Le Baccon, La Rochelle (FR); Olivier Conan, Aytre (FR)

(73) Assignee: Eurekam, Lagord (FR)

( * ) Notice: Subject to any disclaimer, the term of this patent is extended or adjusted under 35 U.S.C. 154(b) by 654 days.

(21) Appl. No.: 16/979,034

(22) PCT Filed: Mar. 5, 2019

(86) PCT No.: PCT/FR2019/050490
§ 371 (c)(1),
(2) Date: Sep. 8, 2020

(87) PCT Pub. No.: WO2019/175492
PCT Pub. Date: Sep. 19, 2019

(65) Prior Publication Data
US 2020/0405957 A1    Dec. 31, 2020

(30) Foreign Application Priority Data

Mar. 13, 2018 (FR) ...................................... 1852147

(51) Int. Cl.
*H04N 7/18* (2006.01)
*H04N 23/51* (2023.01)
(Continued)

(52) U.S. Cl.
CPC ............ *A61M 5/1782* (2013.01); *B65B 3/003* (2013.01); *B65B 57/18* (2013.01); *H04N 7/08* (2013.01);
(Continued)

(58) Field of Classification Search
CPC ...... A61M 5/1782; B65B 3/003; B65B 57/18; B65B 57/10; B65B 59/00; H04N 7/18;
(Continued)

(56) References Cited

U.S. PATENT DOCUMENTS 4,249,413 A * 2/1981 Denis ...................... G01M 3/38
348/125
4,855,821 A    8/1989 Swon
(Continued)

FOREIGN PATENT DOCUMENTS

FR    3007611 A1    12/2014
FR    3007612 A1    12/2014
(Continued)

*Primary Examiner* — Boubacar Abdou Tchoussou
(74) *Attorney, Agent, or Firm* — Harness, Dickey & Pierce PLC

(57) ABSTRACT

A device captures images of a plurality of objects, such as a bottle and a syringe, for the secure production of medicinal preparations. The device includes at least one pair of image capturing cameras, arranged one facing the other; one reflective element for each of the cameras; and the two reflective elements of the same camera pair being arranged between the cameras and each oriented so as to reflect, in the direction of the associated camera, images of a production area of a medicinal preparation. The image capture device additionally includes: a stationary part formed by positioners that are designed to be secured against an enclosure of the medicinal preparation production area, a base which is intended to be secured to the stationary part, and a half-baseplate which is mounted such that it can rotate relative to the base, with the half-baseplate carrying at least one of the cameras.

12 Claims, 6 Drawing Sheets

(51) Int. Cl.
  *H04N 23/55* (2023.01)
  *H04N 23/90* (2023.01)
  *A61M 5/178* (2006.01)
  *B65B 3/00* (2006.01)
  *B65B 57/18* (2006.01)
  *H04N 7/08* (2006.01)

(52) U.S. Cl.
  CPC ............. *H04N 23/51* (2023.01); *H04N 23/55* (2023.01); *H04N 23/90* (2023.01)

(58) Field of Classification Search
  CPC ........ H04N 23/51; H04N 23/55; H04N 23/90; H04N 23/50; H04N 7/181
  See application file for complete search history.

(56) References Cited

U.S. PATENT DOCUMENTS

| | | |
|---|---|---|
| 4,998,570 A | 3/1991 | Strong |
| 5,597,995 A | 1/1997 | Williams et al. |
| 6,011,876 A | 1/2000 | Kishner |
| 7,982,201 B2 * | 7/2011 | Bryant .................. G01F 23/292 250/577 |
| 9,147,334 B2 | 9/2015 | Long et al. |
| 9,305,191 B2 | 4/2016 | Long et al. |
| 10,596,319 B2 * | 3/2020 | Trovato .................. G16H 20/10 |
| 11,637,993 B2 * | 4/2023 | LeFranc .................. H04N 23/51 348/143 |
| 2005/0231341 A1 | 10/2005 | Shimizu |
| 2009/0154764 A1 | 6/2009 | Khan et al. |
| 2010/0245577 A1 | 9/2010 | Yamamoto et al. |
| 2012/0154582 A1 | 6/2012 | Johnson et al. |
| 2015/0029336 A1 | 1/2015 | Kucheryuk |
| 2016/0148056 A1 | 5/2016 | Lefranc et al. |
| 2016/0182944 A1 | 6/2016 | Han et al. |

FOREIGN PATENT DOCUMENTS

| | | |
|---|---|---|
| WO | WO 0225568 | 3/2002 |
| WO | WO 2009/073950 | 6/2009 |

* cited by examiner

ADAPTABLE IMAGE CAPTURE DEVICE AND SYSTEM FOR THE SECURE PRODUCTION OF MEDICINAL PREPARATIONS

CROSS-REFERENCE TO RELATED APPLICATIONS

The application is a National Phase Entry of International Patent Application No. PCT/FR2019/050490, filed on Mar. 5, 2019, which claims priority to French Patent Application No. 1852147, filed on Mar. 13, 2018, both of which are incorporated by reference herein.

BACKGROUND AND SUMMARY

The invention relates to a method for the safe, i.e. controlled and assisted production of medicinal preparations and to an imaging system capable of implementing such a method.

The field of application of the invention relates to the safe manufacture of medicinal preparations allowing for a release authorization test of said preparations. This release authorization test is necessary because medicinal preparations are made according to complex protocols, using reaction mixtures of components, each component having a concentration adapted to a personalized treatment for a given patient. Any error in the nature of a component or its quantity may have serious consequences for the patient to whom the preparation is administered, in particular where a toxic active ingredient is involved, such as cytotoxic preparations which may be used in cancer treatments.

In practice, operators may work several hours in a row, for example in hospital preparation units, which significantly increases the risk of errors in the composition or quantities of components. The safety of the preparations is usually the result of a double visual inspection: verification of the key steps of each preparation and written report on an appropriate traceability form, generally called a "production sheet."

In order to ensure the quality of medicinal preparations, the AFSSAPS (French Agency for the Safety of Health Products) has published "Good Preparation Practices," which is a reference text for pharmacists. The "Good Preparation Practices" specify the three obligations to which the use of raw materials used in medicinal preparations must conform:
the method for measuring the quantities of raw materials is selected according to their nature and the quantity to be measured;
the measurement of the volume or weight of the quantities of raw materials is recorded;
the raw materials are always identifiable during the aforesaid operations.

Thus, during preparation, the nature of each raw material used, as well as the mass or volume thereof, is independently verified either by an automatic recording means or by a second person qualified according to the Public Health Code, and the verification is noted in the batch record of the preparation. In order to comply with "Good Preparation Practices" and for the safety of patients, it is therefore recommended to double-check the nature and quantities of the compositions used in each preparation.

From the applicant's publication WO 2014/202589, a method and image capture device for the safe production of medicinal preparations and a support for the positioning of associated objects is known. With reference to the perspective view in FIG. 1 which reproduces FIG. 1 of the aforesaid publication, the context for monitoring the medicinal preparation developed by the applicant is now recalled.

A portable fume hood 1 incorporates a medicinal preparation site 2. This site 2 is equipped with an imaging system 3 (not shown) allowing such medications to be produced in a secure manner. This imaging system 3 has a camera 4 called a processing camera. The focal length of this camera 4 is set to focus on drug containers and drug delivery tools, here a bottle 5, an infusion bag 6 containing saline, and a syringe 7. In the example, the bottle 5 contains cisplatin for dilution in the infusion bag 6. To do this, the operator withdraws an amount from the bottle 5 of cisplatin using the syringe 7 and then injects it into the infusion bag 6. The operation is repeated until the desired dilution of the active ingredient in the pouch is obtained to prepare, in the example, a multidrug therapy component.

Advantageously, a bottom 8 of the hood 1 has a surface structure shape adapted to the contours of the objects, facilitating a stable and reproducible placement of the bottles and syringes, and integrates a backlighting device 9 allowing a better reading of the gradations of the syringe 7. The processing camera 4 is positioned at the level of the bottom of the hood 8 slightly above a work surface on which the portable hood 1 is placed, i.e. substantially at the stomach level of the operator (not shown) in the example. The processing camera 4 is connected to a digital management unit, in the example a portable computer 11. The computer 11 mainly comprises a processor and memories (not shown) that process video signals Sv1 from the processing camera 4 to provide images to a display screen 12 and record them.

The display screen 12 thus allows the information corresponding to the preparation in progress to be viewed from a video stream Fv1 provided by the processing camera 4. Another recording and viewing camera 13, called a scene camera, has a focal length set for an overall detection of the site 2. The lens of the scene camera 13 is advantageously positioned at an upper level 14 of the hood 1 so as to allow an overall view of the site 2 by transmitting a video stream Fv2 to the display screen 12.

The processing camera 4 and the scene camera 13 provide video signals Sv2 synchronized by the processor of the computer 11 to provide a dynamic graphical interface for real-time and a posteriori inspection. The processing camera 4 is advantageously composed of two adjoined cameras 4a, 4b, with focal lengths adjusted to detect objects—generally bottles and syringes—in compatible size ranges, less than 3 cm and between 3 and 307 cm in the example.

The video streams of the processing cameras 4a and 4b are analyzed by a shape and character recognition tool, integrated in the processor of the computer 11. The analysis allows an automatic identification of the objects used, bottle 5 and syringe 7, by processing the first video streams using the recognition tool. The detection of product volumes contained in the syringes and bottles allows a non-destructive inspection of the active ingredient used in the preparation.

Thus, all the data appearing on the bottle 5, in particular the concentration of the active ingredient, are identified by said recognition tool. These data are stored in the computer 11. During preparation, analysis data of the bottle and syringe contents are displayed on the screen 12 and, for the validation of each step in the preparation, the following are recorded: amount of liquid in the syringe 7 and liquid level in the bottle 5.

The processor of the computer 11 searches for the prescription corresponding to the preparation in progress in a memory where a set of prescriptions is stored. To do this, the stored prescriptions are indexed by steps using a digital indexing tool. The key steps—which are the specific steps for each prescription—have a particular indexation.

The processor compares the stored data for the current preparation provided by the first recorded images—name of the components, quantities poured into the syringes, etc.—and the steps of the stored prescriptions. As soon as a key step in this prescription is recognized, the prescription corresponding to the preparation in progress is then identified and displayed by its steps. The information is selected according to the detected prescription from a list of bottles available and a list of bottles used stored in the computer according to data provided by the laboratory management center.

A warning display is integrated, as well as the possibility of manual interaction to withdraw or inject a specific volume, or to add a bottle. Furthermore, the preparation status is displayed according to the stored protocol data corresponding to the identified prescription: information on the management of the volume contained in the bottle 5 and the progression of the volumes of the component injected/absent/prescribed in the syringe 7 is displayed. This management information is initiated by incrementing the volumes injected and consequently the volume remaining, the number of injections, the number of bottles and the leftovers. This incrementation is automated using the graphical interface of the synchronized video streams from cameras 4 and 13. Such management significantly reduces errors due to manipulations.

The warning display is activated in real time as soon as the bottle and/or component volumes detected before injection in a step do not conform to the stored protocol of the prescription identified. The steps detected in error are identified by comparison with the steps of the prescription. Non-compliance with a key step triggers an error search in the identification of the prescription that has been selected.

The display then provides guidance, the warning is removed, and the preparation continues only if the compliance between the steps of the preparation and those constituting the protocol of said prescription is validated. The progress of the preparation is then updated in real time until the final validation. The preparation is thus made secure by an almost instantaneous responsiveness, and the reproducibility of the preparations is optimized.

The validation of the steps detected in error, in particular the key steps of the preparation, makes it possible to continue the preparation until its completion. Thus, the preparation may be done under a stationary hood or any environment suitable for the installation of the imaging system.

With reference to FIGS. 2 to 7, which are based on FIGS. 4 to 9 of the aforementioned publication, an example of an imaging system implementing the method for the secure production of medicinal preparations is described. This system is arranged on both sides of a transparent bay 15 of a secure production enclosure for a medicinal preparation, and comprises an image capture device 16 arranged on the outside of the enclosure against the transparent wall 15, and an object positioning support 17 arranged within the enclosure opposite the image capture device.

More precisely, as best seen in FIG. 4, the image capture device 16 comprises two processing cameras 18, 19 arranged at either end of an elongated rectangular baseplate 20, with a reflective element 21, 22 for each of the image capturing cameras 18, 19 arranged at the mid-length of the baseplate 20. The two reflective elements 21, 22 are oriented along the axis defined by the two cameras, so as to reflect images of the object positioning support 17 in the direction of the corresponding camera. More precisely, these two reflective elements are formed by the two adjacent rectangular faces of a straight prism with a triangular base 23, the prism being mounted on the baseplate by one of the triangular bases thereof.

The two cameras 18, 19 have lenses with different focal lengths to focus on objects of different sizes arranged on the syringe and bottle support. For example, the camera on the right with a 12 mm lens may be used to focus on small bottles and syringes, while the camera on the left with an 8 mm lens may be used to focus on large bottles and syringes. In order to give the image capture device small dimensions, the two cameras will themselves be small, e.g., 47×29×29 mm (L×W×H). An example of cameras suitable for this use is the Imaging Source® brand, part number DFK23F445.

The elongated baseplate 20 is secured within a case 24 comprising a flat and substantially rectangular front face 25, of which two short sides are slightly rounded; and provided with a substantially rectangular central viewing window 26, and an elongated rear shell 27 within which the baseplate 20 is integrally secured by its longitudinal rear edge, the prism 23 being located in the opening of the window 26 when the front face 25 of the case closes the shell 27, so that the images of the syringe and bottle support reach the two cameras 18, 19 via this prism. The front face 25 may be secured to the shell 27 by means of screws passing through holes 28 provided for this purpose at the four corners of the front face 25 and screwing into a corresponding sheath 29 provided for this purpose on the inner wall of the rear shell 27. The back shell 27 further comprises two feet 30 extending vertically from the lower side edge 31 thereof, said feet being provided with a central circular recess for accommodating a magnetic means with a compatible shape (metal or magnetic disc, not shown), intended to retain the syringe and bottle support 17, which is provided with compatible magnetic means, against the glass bay 15 and the front face 25 of the case. The shell 27 further comprises two rigid side slats 32 secured to the outside of the rear wall thereof and projecting from either side of the ends thereof, these two slats 32 having two forward-facing suction cups 33 to be secured to the glass bay of the enclosure.

On the other hand, according to FIG. 5, the syringe and bottle support 17 comprises a flat support base 34, an inclined screen 35 set up behind the base to form a white background, and a syringe holder 36 mounted so as to be translatable relative to the base 34 between a disengaged position independent of the base 34 (illustrated in FIG. 5) and an engaged position integral with the base 34 (illustrated in FIG. 2). More precisely, the syringe holder 36 comprises a rectangular plate 37 from one end of which protrudes a block 38 with a substantially rectangular shape but having a longitudinally recessed top wall 39 (the top wall is composed of sloping sides converging towards each other and joined by a common edge, defining an M-shaped cross section) in order to serve as a support for the body of a syringe, and to hold said syringe body laterally by the sloping sides. At the other end, the plate 37 of the syringe holder 36 comprises a stand 40 for holding the wings 41 of a syringe 42. The stand 40 is formed by two parallel walls, separated from each other by a sufficient distance to accommodate the wings 41 of the syringe 42 (see FIG. 6), and having, like the block 38, an M-shaped contour to support and retain the syringe portion laterally near the wings 41.

According to FIG. 7, an additional stand 43 is provided to support small syringes between the block 38 and the main stand 40, being closer to the block 38, and having the form of a single wall 43 with an M-shaped contour, the groove of which is at the same level as that of the block 38. The plate 37 of the syringe holder 36 comprises, as shown in FIG. 5, two tapered side edges 44 able to slide into grooves formed on the side edges of a recess for receiving the plate arranged in the base 34, so that the syringe support may engage by sliding in the base into an engaged position (FIG. 2). In this engaged position, the syringe support 36 and the base 34 together define a protuberance 45 for receiving the bottom of a bottle. In effect, the upper surfaces of the base 34 and the plate 37 of the syringe holder 36 are coplanar when the syringe holder is in its engaged position and comprise compatible half-disc-shaped recesses 45 for accommodating a bottle, and which, when the syringe holder is in its engaged position, form a circular recess for receiving the bottom of a bottle, this recess being arranged between the retaining stand 40 and the support block 38. Naturally, another protuberance, such as a circular rib, may perform the same function.

The base 34 has magnetic means 46 compatible with those provided on the feet 30 of the image capture device. More precisely, these magnetic means (magnetic or metallic disc, according to the one used for the magnetic means of the image capture device) are housed inside two lugs 47 projecting vertically from the edge of the base 34 opposite the screen 35, and having a flat front wall which may be pressed against the inner face of the glass bay at the level of the corresponding feet 30 of the image capture device.

The system as described above allows the implementation of the method for the secure production of medicinal preparations, even when syringes and bottles of different sizes are used, due to the plurality of image capturing cameras with different lenses used and the reflective elements allowing these cameras to capture images from the same area: the syringe and bottle support. This object is further achieved with a small footprint due to the use of a central prism for the two image capturing cameras. However, the applicant has continued to innovate.

The applicant noted that its system was not suitable for use with different inclinations of transparent bays in relation to the work surface. In effect, between two predetermined sites on which the medicinal preparation must be carried out, the inclinations of the bays may be different, forcing the applicant to adapt its system to each of the inclinations of the bays. The applicant further noted that the positioning of the system described in the aforesaid publication could be imprecise, in particular due to the use of suction cups. In effect, a calibration is required at installation. The cleaning of the bay 15 may require the removal of the image capture device and therefore its suction cups. It is thus difficult to reposition it in the same way, which may lead to image capture problems. The applicant also noted that the operators are subject to musculoskeletal disorders (MSDs) and that the presence of the screen involves a movement that causes tendonitis of the rotator cuff of the operator's shoulder when the operator uses the product.

One object of the invention is, in particular, to remedy all or some of the aforesaid drawbacks. According to a first aspect of the invention, an image capture device for a plurality of objects such as a bottle and a syringe is proposed, with a view to the safe production of medicinal preparations, comprising:
at least one pair of image capturing cameras arranged opposite each other,
a reflective element for each of the image capturing cameras, the two reflective elements of a same pair of cameras being arranged between said cameras and each oriented so as to reflect images of a production area of a medicinal preparation towards the corresponding camera,
characterized in that the image capture device further comprises:
a stationary part formed by positioning means intended to be secured against an enclosure in the production area of the medicinal preparation,
a base intended to be secured to the stationary part, and
a half-baseplate mounted rotatably relative to the base, the half-baseplate comprising at least one of the image capturing cameras.

Also, it becomes possible to use the same device with different inclinations of the transparent bays in relation to the work surface. Advantageously, the device according to the invention may further comprise means for selecting the angle formed between the base and the half-baseplate. The stationary part may be designed to be permanently secured to the enclosure of the production area of the medicinal preparation.

The removable part may be designed to be removably attached to the stationary part; said removable part may comprise the base and the half-baseplate. The positioning means may cooperate with compatible magnetic means arranged on the removable part.

According to one possibility the two areas covered by the two cameras in a same camera pair are spatially offset, and the cameras have lenses with different focal lengths to focus on objects of different sizes in the production area of the medicinal preparation. According to an embodiment, the removable part comprises a cover which is itself removable with respect to said removable part. It then becomes possible to set different parameters for the cameras as well as their angular position, without having to dismantle the whole system, which was not possible according to the prior art. By way of example, the two reflective elements may be formed by flat surfaces.

According to a second aspect of the invention, a secure imaging system is provided, comprising an imaging device according to the first aspect of the invention, or one or more of the improvements thereof, an object positioning support, installed on an enclosure for the production of medicinal preparations, the object positioning support being arranged within the enclosure, and the image capture device outside of the latter against a transparent bay of the enclosure, and in a position such that images of the object positioning support reach the image capturing cameras of the device. Advantageously, the positioning support may comprise means for securing the object positioning support which are magnetic means cooperating, through the medicinal preparation enclosure, with the positioning means arranged on the stationary part of the image capture device. Preferably, the fastening means of the object positioning support are magnetic means which cooperate with the compatible magnetic means arranged on the removable part of the image capture device. By way of example, the object positioning support may further comprise a flat base for supporting objects and a screen set up behind the flat base, the screen being removable relative to the flat base, the screen comprising magnetic means compatible with magnetic means housed in the flat base.

BRIEF DESCRIPTION OF THE DRAWINGS

Other data, features and advantages of this invention will appear on reading the description of implementations and embodiments, which are in no way limiting, in view of the accompanying drawings wherein.

DETAILED DESCRIPTION

Figure 1:
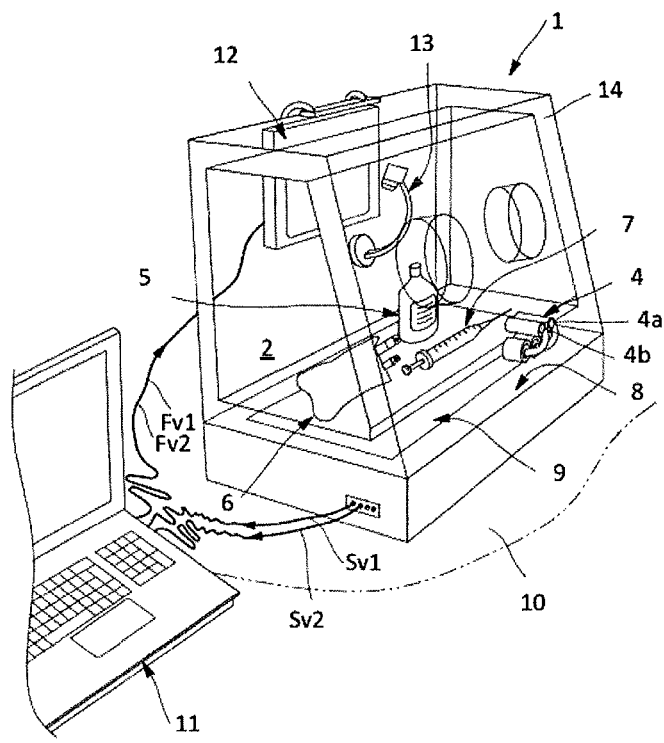
FIG. 1 is a perspective view of a medicinal preparation site equipped with an example of a secure imaging system for such medicinal preparations.
Figure 2:
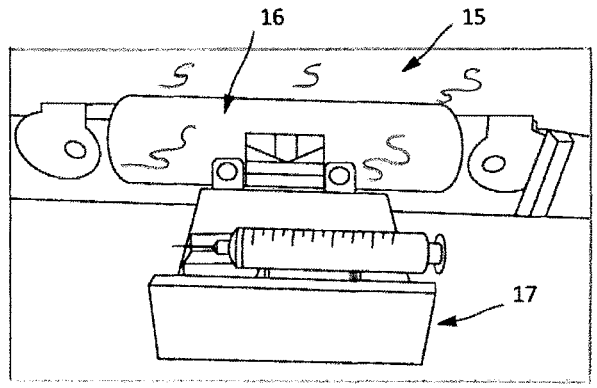
FIG. 2 is a front perspective view of an image capture system for syringes and bottles of different sizes, positioned on the transparent bay of a preparation enclosure, a support for syringes and bottles, within the enclosure, and an image capture device outside of the enclosure.
Figure 3:
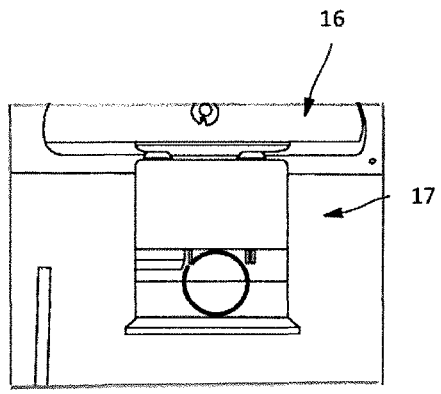
FIG. 3 is a top perspective view of the system in FIG. 2.
Figure 4:
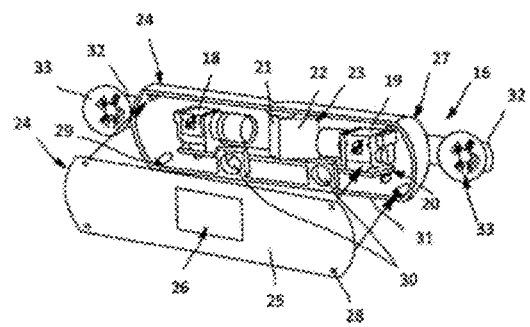
FIG. 4 is an exploded view of the device in FIG. 2.
Figure 5:
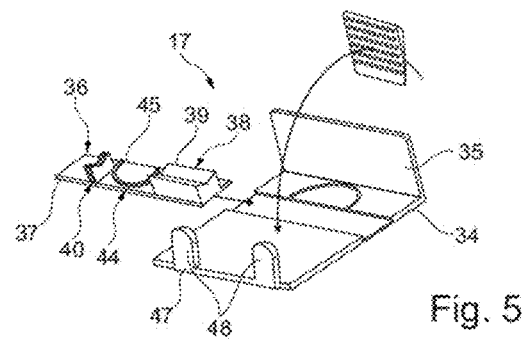
FIG. 5 is an exploded view of the syringe and bottle support in FIG. 2; showing a syringe holder in a disengaged position relative to a base of the support.
Figure 6:
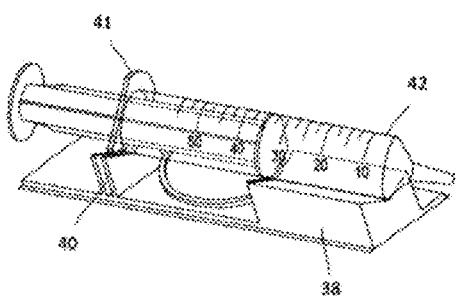
FIG. 6 is a perspective view of the right side of the support holding a syringe.
Figure 7:
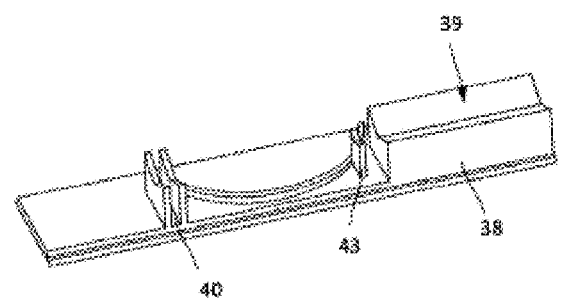
FIG. 7 is a perspective view of the left side of the support without a syringe.
Figure 8:
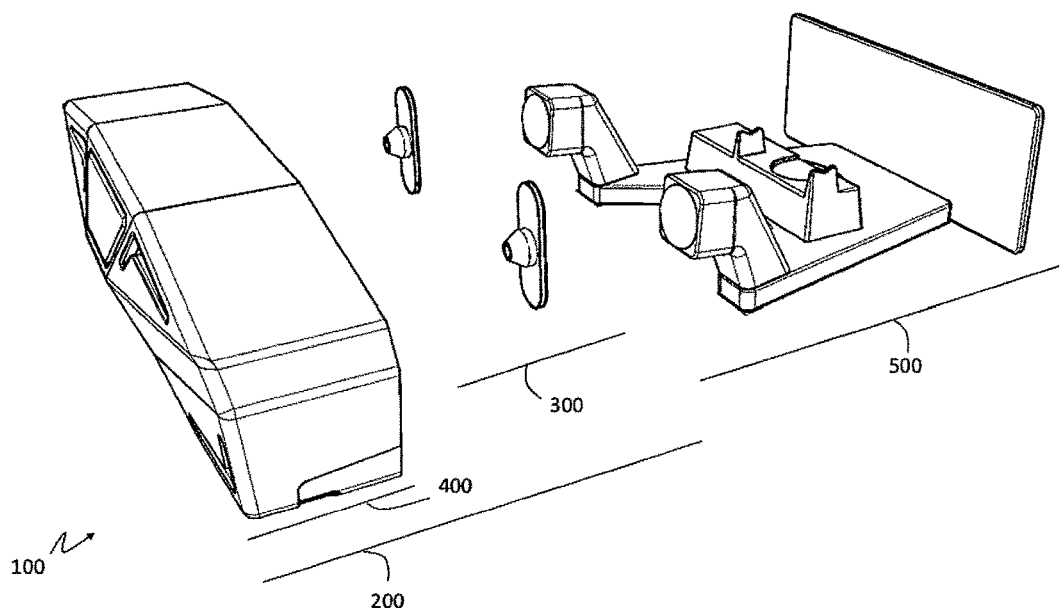
FIG. 8 is a perspective view from the front, top and right side of an exploded view of a system according to the invention.

Since the embodiments described hereinafter are by no means limiting, one may in particular consider variants of the invention comprising only a selection of features described, subsequently isolated from the other features described, if this selection of features is sufficient to confer a technical advantage or to differentiate the invention in relation to the prior art. This selection comprises at least one feature, preferably functional without structural details, or with only a part of the structural details if that part alone is sufficient to confer a technical advantage or to differentiate the invention from prior art.

With reference to FIGS. 8 to 14, an example of an image capture system 100 implementing the previously described method for the secure production of medicinal preparations is now described. As previously described, this system is adapted to be arranged on either side of a transparent bay 15 of a secure enclosure for the production of a medicinal preparation. The system comprises an image capture device 200 arranged outside the enclosure against the transparent wall 15, and an object positioning support 500 arranged within the enclosure opposite the image capture device 200.

Specifically, the image capture device 200 comprises:

a stationary part 300 intended to be permanently secured to the transparent bay 15 of the production area of the medicinal preparation, a removable part 400, intended to be removably secured to the stationary part 300.

The image capture system 100 comprises a main vertical plane of symmetry and, in said longitudinal direction, comprises, successively, from front to rear, the device 200 and the device 500.

Figure 9:
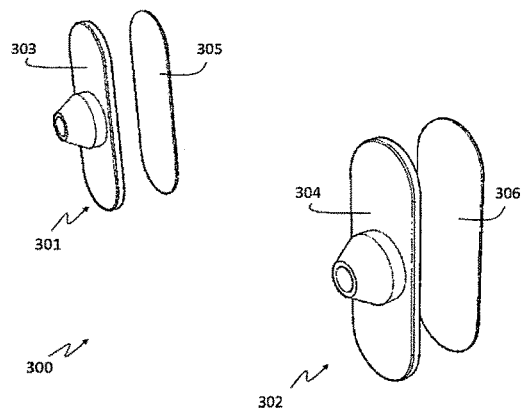
FIG. 9 is a perspective view from the front, top and right side of an exploded view of a stationary part of an image capture device of the system according to the invention.

With reference to FIG. 9, the stationary part 300 will now be described. It comprises two positioning means 301 and 302 intended to be permanently secured on the transparent bay 15. By convention, the positioning means 301 is said to be positioned on the left and the positioning means 302 is said to positioned on the right. Each of the two positioning means 301, 302 respectively, has a magnetic stainless steel pad 303, 304 respectively.

"Magnetic stainless steel pad" in this description refers to a pad made of magnetic stainless steel, for example of the ferritic or martensitic type. The magnetic stainless steel pads are intended to be permanently secured to the outside of the bay 15. For this purpose, each of the two assemblies 301, 302 respectively, comprises a double-sided adhesive 305, 306 respectively, of the same oblong shape as the magnetic stainless steel pad 303, 304 respectively. One side of the adhesive 305, 306 respectively is bonded to the stainless steel magnetic pad 303, 304 respectively. The other side of the adhesive 305, 306 respectively, is intended to be bonded to the outside of the transparent wall 15.

Figure 10:
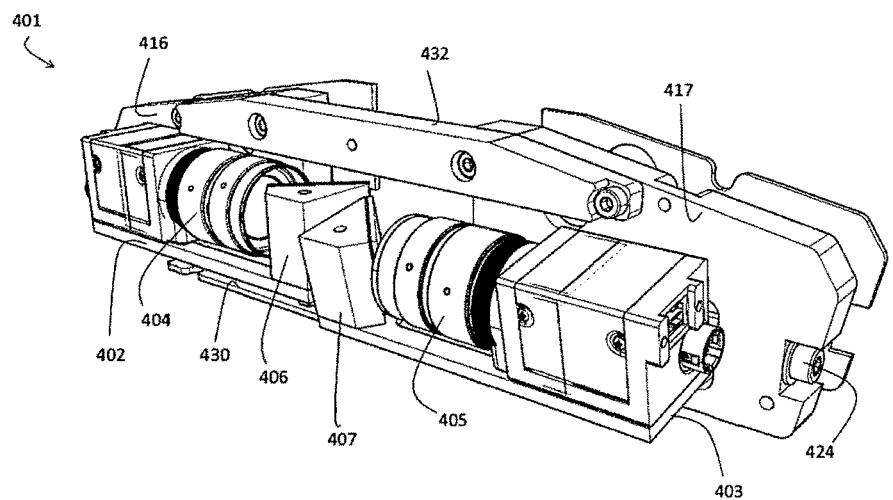
FIG. 10 is a front and right perspective view of a mechanical sub-assembly of a removable part of the image capture device.
Figure 11:
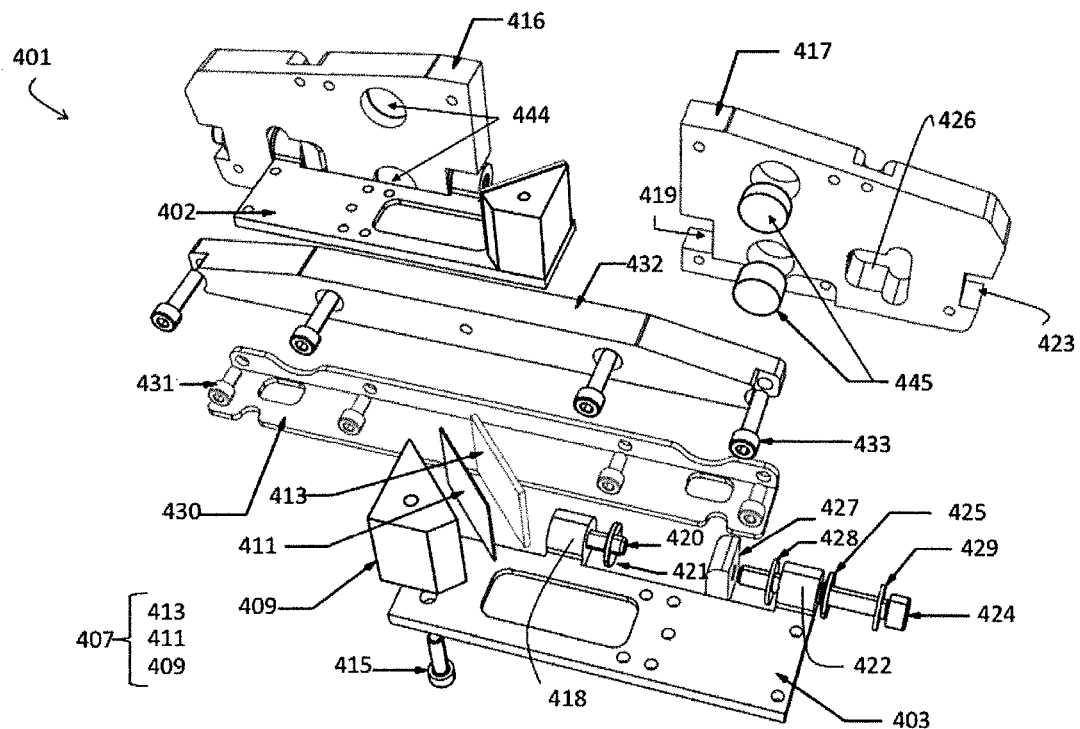
FIG. 11 is an exploded schematic representation of the mechanical sub-assembly also shown in FIG. 10.

As best seen in FIGS. 10 to 11, the removable part 400 has an inner mechanical assembly 401. The inner mechanical assembly 401 comprises two elongated rectangular half-baseplates 402 and 403, left and right respectively. Each of the two half-baseplates, 402 and 403 respectively, is provided to receive a processing camera, 404 and 405 respectively, and a reflective element, 406 and 407 respectively, for each of the image capturing cameras 404, 405.

Figure 12:
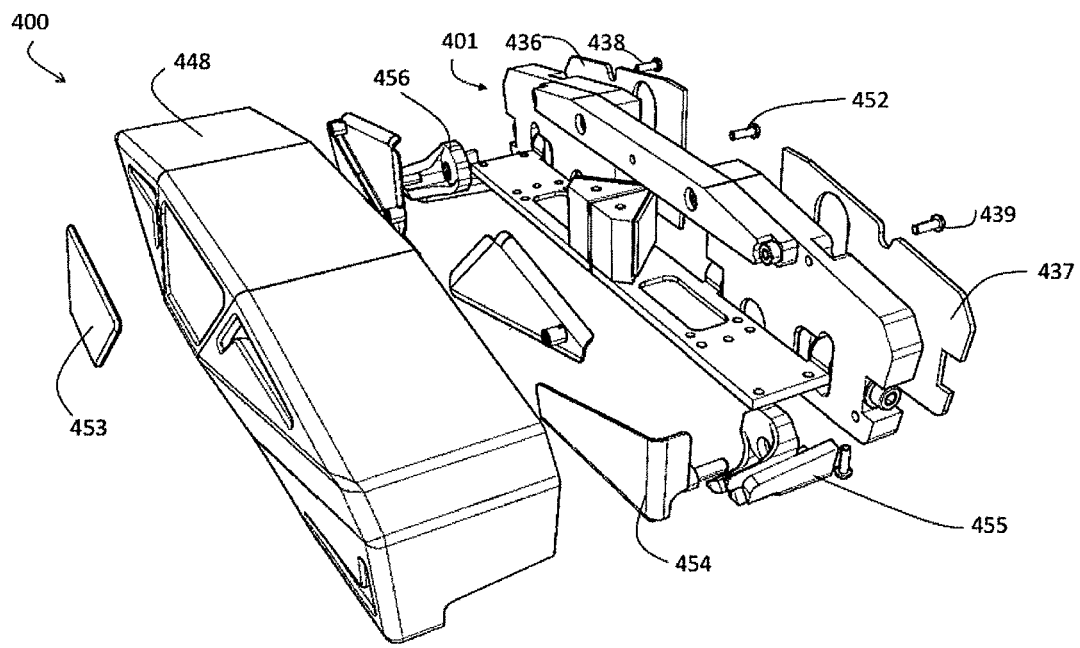
FIG. 12 is a perspective view of the front, top and right side of an exploded view of the removable part of the image capture device according to the invention.

In a position as shown in FIG. 12, the two half-baseplates 402 and 403 are arranged side by side along one of their widths, with the half-baseplate 402 to the left of the half-baseplate 403:

the processing camera 404 is arranged on the left end of the half-baseplate 402 and is oriented to the right, the processing camera 405 is arranged on the right end of the half-baseplate 403 and is oriented to the left, the two reflective elements 406 and 407 are located respectively on the right and left of the half-baseplate 402 and 403.

The two reflective elements, 406 and 407 respectively, are oriented so as to reflect images of the object positioning support 500 towards the corresponding camera, 404 and 405 respectively. Even more precisely, with reference to FIG. 11, the reflective element 407 comprises a rectangular-sided main support 409 which is bonded with a double-sided adhesive 411, which in turn is bonded to a mirror 413. The reflective element 407 is secured to the half-baseplate 403 with a screw 415, making it possible to adjust the angle of the main support 409 relative to an axis perpendicular to the half-baseplate 403. The reflective element 406 is composed of similar elements in symmetry relative to the main plane of symmetry.

The two cameras 404, 405 have lenses with different focal lengths allowing for focus on objects of different sizes located on the syringe and bottle support. For example, the camera on the right with a 12 mm lens may be used to focus on small bottles and syringes, while the camera on the left with an 8 mm lens may be used to focus on large bottles and syringes. In order to give the image capture device small dimensions, both cameras will themselves be small, e.g. 47×29×29 mm (L×W×H). An example of cameras suitable for this use is the Imaging Source® brand, reference number DFK23F445.

Each of the half-bases, 402 and 403 respectively, is rotatably mounted along an axis perpendicular to the main plane of symmetry, and arranged on a rear part and above its baseplate, on a base, respectively a left base 416 and a right base 417. The connection between the right baseplate 403 and the right base 417 is formed by two pivot connections on the same axis, the two connections being held axially in abutment.

A first eyelet 418 attached to the baseplate 403, on the left side of the baseplate 403, and a first axle housing 419 formed on the right base 417, on the left side of the right base 417, cooperate with a pin 420 to form a first hinge between the baseplate 403 and the right base 417. A washer 421, preferably conical and grooved, is arranged radially about the pin 420, between the first eyelet 418 and the axle housing 419. The right base 417 comprises a housing for the first eyelet 418.

A second eyelet 422 attached to the baseplate 403 on the right side of the baseplate 403, and a second axle housing 423 attached to the right base 417 on the right side of the right base 417, cooperate with a screw 424 to form a second hinge between the baseplate 403 and the right base 417. A washer 425, preferably conical and grooved, is arranged radially about the screw 424, between the second eyelet 422 and the axle housing 423. The right base 417 comprises a housing 426 for the axle housing 422.

The housing 426 is further shaped to accommodate a captive nut 427 which receives the screw 424. A washer 428, preferably nylon, is provided to be mounted radially about the screw 424, between the captive nut and the second eyelet 422. Another washer 429, preferably nylon, is provided to be mounted radially about the screw 424, between the axle housing 423 and the head of the screw 424. In the same way, the linkage between the left baseplate 402 and the left base 416 is formed by two pivot connections on a same axis, the two connections being held axially in abutment.

It is understood that the screw 424 and the nut 427 form a means for adjusting the angular position of the right half-baseplate 403 relative to the right base 417. The angular position of the left half-baseplate 402 relative to the left base 416 is also adjustable, for example by means of a screw and a captive nut. The inner mechanical assembly 401 further comprises an elongated, rectangular lower connecting arm 430. The lower connecting arm 430 is firmly secured, by a longitudinal rear edge, to the bottom of each of the bases, left base 416 and right base 417 respectively, on the front side of the base, by means of fastening elements, such as screws 431.

The inner mechanical assembly 401 further comprises a top connecting arm 432. The top connecting arm 432 is firmly secured, at the top of each of the bases, left base 416 and right base 417 respectively, on the front side of the base, by means of fastening elements, such as screws 433. The front side of the base is the side on which the cameras are located relative to the plane of the base.

Figure 13:
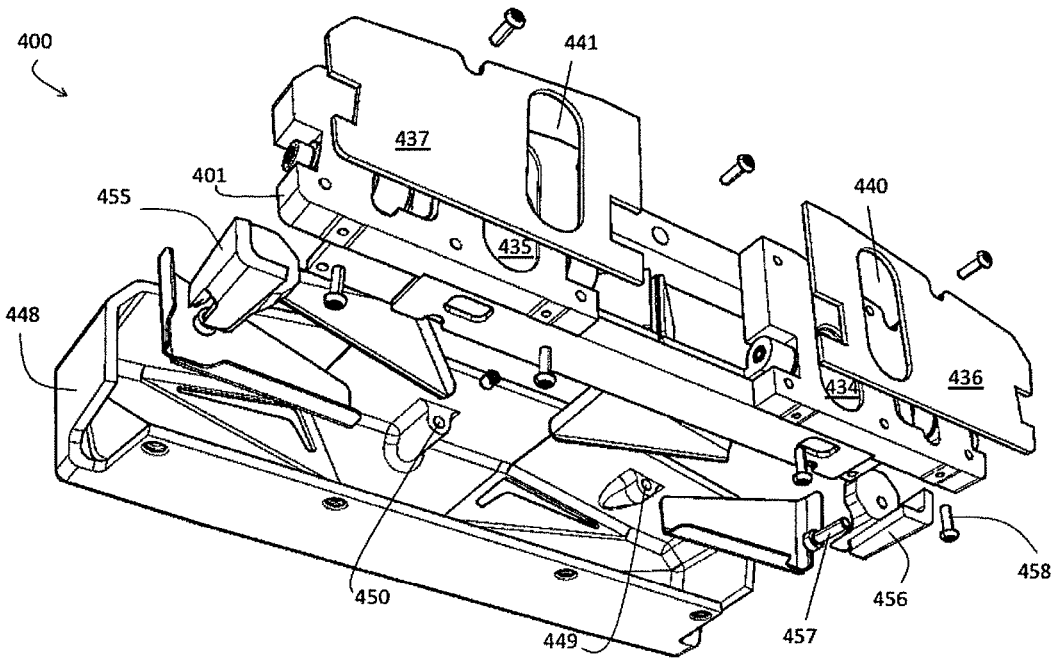
FIG. 13 is a perspective view of the back, bottom, and right side of the exploded view also shown in FIG. 12.

As may be better seen in FIG. 13, each of the bases 416, 417 respectively, has, on the rear side of the compartment, a vertical housing 434, 435 respectively, with an oblong shape having a truncated cone-shaped centering hole in its center, with an axis perpendicular to the oblong shape. The mechanical image capture device 400 further has two foam plates, right 436 and left 437 respectively, of the same section as the rear section of the left base 416 and the right base 417. Each of the foam plates, right 436 and left 437 respectively, is secured to the rear side of its base, left base 416 and right base 417 respectively, by means of an adhesive.

Each of the foam plates, right 436 and left 437 respectively, has a window, 440 and 441 respectively, with a shape cooperating with the oblong shape of the associated vertical housing, 434 and 435 respectively. The mechanical image capture device 400 also has a cover 448 with a front, top and bottom face, as well as left and right side faces. The cover 448 is arranged to house the inner mechanical assembly 401. For this purpose, the rear face of the front face has, in its top part, three housings 449, 450, 454 (not referenced in the figures), with inserts, perpendicular to the front face of the image capture device, and extending rearwards.

Screws 438 and 439 (FIG. 12) pass through the mechanical assembly 401 from back to front and are screwed, respectively, into the housings with inserts 449 and 451. A screw 452 passes through the mechanical assembly 401 from back to front and is screwed into the sheath 450. With reference to FIG. 9, each of the two assemblies 301, 302 respectively cooperates mechanically with the vertical housing 434, 435 respectively, through the foam plate, right 436 and left 437 respectively, to hold the removable part 400 of the image capture device 200 in engagement and to be retracted when it is against the outside of the transparent wall 15.

Each stainless steel magnetic pad 303, 304 respectively, cooperates mechanically with the vertical housing 434, 435 respectively. Each magnetic stainless steel pad 303, 304 respectively, cooperates magnetically with two sets of magnets, 444 and 445 respectively, accommodated in housings in each of the bases, 416 and 417 respectively, towards the front of the removable part 400, relative to the housings 434 and 435. The front panel has a support on which a logo plate 453 is bonded.

In addition, the front face has four ventilation openings. Filters 454 are arranged inside the cover 448 and against the ventilation openings. The front face is notched to provide two places for corner inserts. Two types of corners that may be inserted in the places are provided. In the example shown, a corner 455 with a grommet is provided to be placed on the right side. A corner 456 without a grommet is provided to be placed on the left side. Each of the corners is secured to the mechanical assembly 401 by means of a stainless steel screw 457. The cover is further secured to the inside of the left base 416 and the right base 417 respectively, by means of tamper-proof screws 458.

Figure 14:
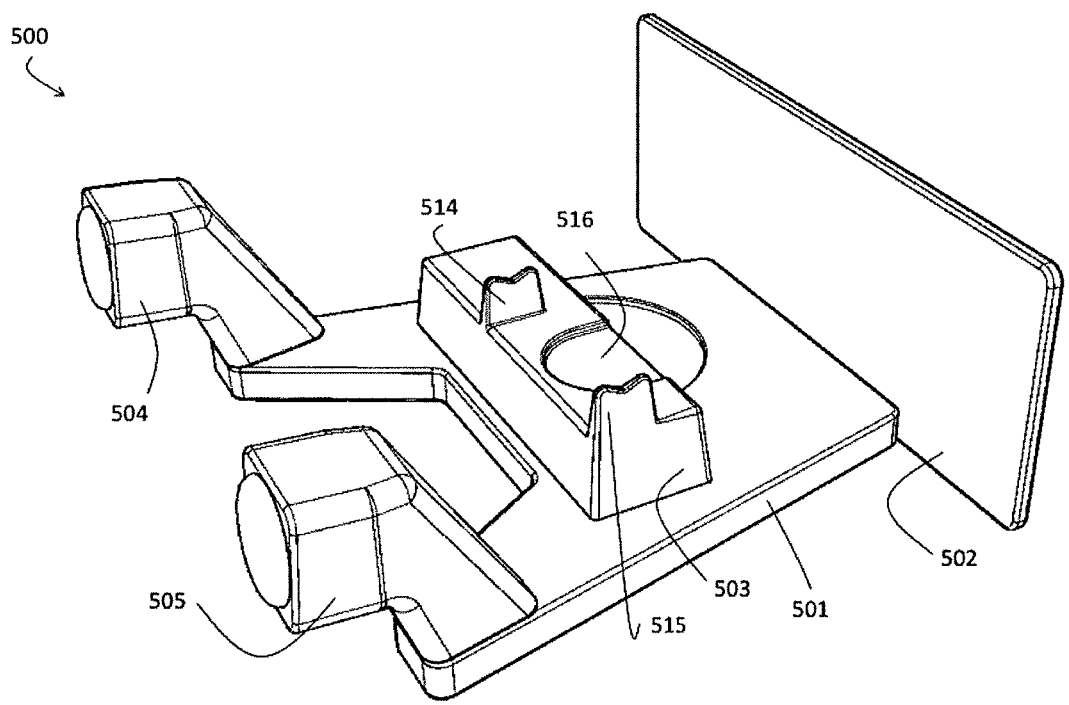
FIG. 14 is a perspective view of the front, top and right side of an object support of the system according to the invention.
Figure 15:
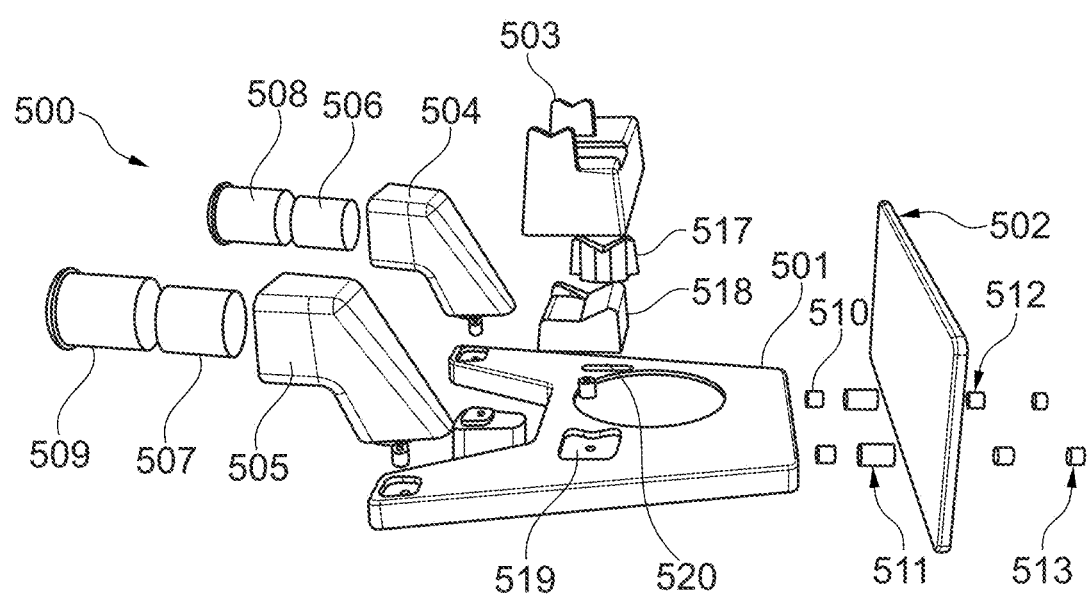
FIG. 15 is a perspective view of the right side of an exploded view of the object support also shown in FIG. 14.

FIGS. 14 and 15 show the object positioning support 500. The object positioning support 500 comprises a flat support base 501, a screen 502 set up behind the base 501 intended to form a white background, an adapter 503 for small objects, mounted on the base 501 and two feet, right 504 and left 505 respectively, extending vertically at the front of the base 501 and intended to come to rest against the inner wall of the bay 15. The left foot 504 and right foot 505 carry magnetic means, such as magnets, 506 and 507 respectively, compatible with the two sets of magnets, 444 and 445 respectively.

More precisely, these magnetic means (magnetic or metallic disc, according to the one used for the magnetic means of the image capture device) are housed inside two lugs 508 and 509 having a rounded front wall which may be placed against the inner face of the glass bay, at the level of these magnetic means 444 and 445 of the image capture device. The roundness of the wall allows a point contact, which allows a minimum distance between the magnetic means and the magnetic stainless steel pad. Thus, the positioning of the support 500 in relation to the image capture device 200 is precise.

The screen 502 is removably mounted relative to the base 501, by means of magnets 510 housed in cages 511 of the base 501, compatible with magnets 512 housed in plugs 513 of the screen 502. The adapter 503 for small objects has a substantially rectangular block shape comprising two stands 514, 515, defining an M-shaped cross-section, for serving as a support for the body of a syringe, and for laterally retaining said syringe body by the inclined sides. The adapter 503 further comprises a housing 516 for the bottom of a bottle arranged between the two stands.

The adapter 503 is removably positioned on the base 501 by means of two feet, 517 and 518 respectively, extending vertically, which are housed in two housings formed in the base 501, 519 and 520 respectively. When the adapter 503 is removed, the feet 517 and 518 are themselves stands, defining an M-shaped cross-section, to serve as a support for the syringe body and to hold this syringe body laterally by the sloping sides. The feet 517 and 518 are preferably used to support large syringes.

In addition, the adapter 503 comprises a reference element, such as a barcode, which is, for example, arranged on a front part and visible by a camera. The presence or absence of the reference element may be detected by a processing unit and selects a particular processing mode.

Naturally, the invention is not limited to the examples just described and numerous adjustments may be made to these examples without going beyond the scope of the invention. Moreover, the different features, forms, variants and embodiments of the invention may be associated with each other in various combinations insofar as they are not incompatible or exclusive of each other.

The invention claimed is:

1. An image capture device for a plurality of objects, for the safe production of medicinal preparations, comprising:
    (a) at least one pair of image capturing cameras arranged opposite each other;
    (b) a reflective element for each of the image capturing cameras, the two reflective elements of the same camera pair being arranged between the cameras and each oriented so as to reflect images of a production area of a medicinal preparation towards the corresponding camera, the image capture device further comprising:
    a stationary part secured against an enclosure in the production area of the medicinal preparation;
    a base secured to the stationary part; and
    a half-baseplate mounted rotatably relative to the base, the half-baseplate comprising at least one of the image capturing cameras.

2. The device according to claim 1, further comprising a fastener operably used to select an angle formed between the base and the half-baseplate.

3. The device according to claim 1, wherein the stationary part is permanently secured to the enclosure of the production area of the medicinal preparation.

4. The device according to claim 1, comprising a removable part removably secured to the stationary part, the removable part comprising the base and the half-baseplate.

5. The device according to claim 1, further comprising positioning means cooperating with a compatible magnet arranged on the removable part.

6. The device according to claim 1, wherein the two areas covered by the two cameras of the same camera pair are spatially offset, and wherein the cameras have lenses with different focal lengths for focusing on objects of different sizes located in the production area of the medicinal preparation.

7. The device according to claim 4, wherein the removable part comprises a cover which is itself removable relative to the removable part.

8. The device according claim 1, wherein the two reflective elements are formed by flat surfaces.

9. A secure imaging system comprising an image capture device and an object positioning support configured to be located in a medicinal preparation production enclosure, the object positioning support being arranged inside the enclosure and the image capture device outside of the enclosure thereof against a transparent bay of the enclosure and in a position such that images from the object positioning support reach the cameras of the device, the image capture device comprising:
    image capturing cameras arranged opposite each other;
    a reflector associated with each of the image capturing cameras, the reflectors of a pair of the cameras being arranged between the pair of the cameras and each oriented so as to reflect images of a production area of a medicinal preparation towards the corresponding camera;
    a stationary portion secured against an enclosure in the production area of the medicinal preparation;
    a base secured to the stationary portion; and
    a half-baseplate mounted rotatably relative to the base, the half-baseplate comprising at least one of the image capturing cameras.

10. The system according to claim 9, wherein the positioning support comprises a magnet cooperating, through the medicinal preparation enclosure, with a positioner arranged on the stationary portion of the image capture device.

11. The system according to claim 9, wherein the object positioning support further comprises a fastener cooperating with a compatible magnetic member arranged on the removable part of the image capture device.

12. The system according to claim 9, wherein the object positioning support further comprises a flat base supporting objects and a screen set up behind the flat base, the screen being removable relative to the flat base, the screen comprising magnetic means compatible with magnetic means housed in the flat base.

* * * * *